US00PP14167P29

(12) United States Plant Patent
Rijnbeek

(10) Patent No.: US PP14,167 P2
(45) Date of Patent: Sep. 23, 2003

(54) VERBASCUM PLANT NAMED 'ROSIE'

(76) Inventor: Nicolaas A. M. Rijnbeek, Reijerskoop 303, 2771 BL Boskoop (NL)

( * ) Notice: Subject to any disclaimer, the term of this patent is extended or adjusted under 35 U.S.C. 154(b) by 0 days.

(21) Appl. No.: 10/142,843

(22) Filed: May 10, 2002

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Verbascum plant named 'Rosie', characterized by its upright and outwardly spreading plant habit; and light pink-colored flowers with red purple-colored centers.

1 Drawing Sheet

Botanical classification/cultivar designation: *Verbascum L.* cultivar Rosie.

BACKGROUND OF THE INVENTION

The present Invention relates to a new and distinct cultivar of Verbascum plant, botanically known as *Verbascum L.,* and hereinafter referred to by the cultivar name Rosie.

The new Verbascum was discovered by the Inventor as a naturally occurring whole plant mutation of the *Verbascum L.* cultivar Jackie, not patented. The new Verbascum was discovered by the Inventor on July 20, 2001 in a controlled environment in Boskoop, The Netherlands.

Asexual reproduction of the new cultivar by divisions in Boskoop, The Netherlands, has shown that the unique features of this new Verbascum are stable and reproduced true to type in successive generations.

SUMMARY OF THE INVENTION

Plants of the cultivar Rosie have not been observed under all possible environmental and cultural conditions. The phenotype may vary somewhat with variations in environment such as temperature and light intensity without, however, any variance in genotype.

The following traits have been repeatedly observed and are determined to be the unique characteristics of 'Rosie'. These characteristics in combination distinguish 'Rosie' as a new and distinct cultivar:

1. Upright and outwardly spreading plant habit.
2. Light pink-colored flowers with red purple-colored centers.

Plants of the new Verbascum can be compared to plants of the parent cultivar, Jackie. In side-by-side comparisons conducted in Boskoop, The Netherlands, plants of the new Verbascum differed from plants of the cultivar Jackie primarily in flower color as plants of the cultivar Jackie had light orange-colored flowers.

BRIEF DESCRIPTION OF THE PHOTOGRAPHS

The accompanying colored photographs illustrate the overall appearance of the new Verbascum, showing the colors as true as it is reasonably possible to obtain in colored reproductions of this type. Colors in the photographs may differ slightly from the color values cited in the detailed botanical description which accurately describe the colors of the new Verbascum.

The photograph at the top of the sheet comprises a side perspective view of a typical flowering plant of 'Rosie' grown in an outdoor nursery.

The photograph at the bottom of the sheet comprises a close-up view of the upper surface (left) and lower surface (right) of typical flowers of 'Rosie'.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photograph and for the following description were about two years old and grown under outdoor field conditions which closely approximate commercial production conditions in Boskoop, The Netherlands. The photographs and description were taken in August, 2001.

Botanical classification: *Verbascum L.* cultivar Rosie.
Parentage: Naturally-occurring whole plant mutation of the *Verbascum L* cultivar Jackie, not patented.
Propagation:
*Type.*—By divisions.
*Root description.*—Fibrous, fine; light brown in color.
Plant description:
*Form.*—Perennial flowering plant; upright and outwardly spreading plant habit; foliage arranged in a basal rosette; moderately vigorous growth habit.
*Plant height.*—About 40 cm.
*Plant diameter.*—About 60 cm.
*Basal stem description.*—Length: About 50 cm. Diameter, base: About 3.5 mm. Internode length: About 2 cm. Strength: Strong. Texture: Pubescent. Color: 143A to 143B.
*Foliage description.*—Arrangement: Alternate, simple. Length: About 15 cm. Width: About 5 cm. Shape: Oblong to elliptic. Apex: Broadly acute. Base: Attenuate. Margin: Crenate. Texture, upper and lower surfaces: Pubescent; rugose. Venation pattern: Pinnate. Petiole: Length: About 4.5 cm. Diameter: About 3 mm. Texture, upper and lower surfaces: Pubescent. Color: Young foliage, upper surface:

137A. Young foliage, lower surface: 138A. Fully expanded foliage, upper surface: Slightly darker than 137A. Fully expanded foliage, lower surface: 138A. Venation, upper and lower surfaces: 138B to 138C. Petiole: 138B to 138C.

Flower description:

*Appearance.*—Single rotate flowers with five petals arranged on terminal racemes. Flowers slightly cupped and face mostly outwardly. Flowers not persistent.

*Quantity of flowers.*—About 40 flowers develop per raceme.

*Natural flowering season.*—Plants flower continuously from late May to late August in Boskoop, The Netherlands.

*Fragrance.*—None detected.

*Flower longevity.*—About four days.

*Inflorescence length.*—About 35 cm.

*Inflorescence diameter.*—About 15 cm.

*Flower diameter.*—About 3 cm.

*Flower depth (height).*—About 1 cm.

*Flower buds.*—Length: About 6 mm. Diameter: About 7 mm. Shape: Flattened globular. Color: 65A.

*Petals.*—Quantity per flower: Five; fused at the base. Arrangement: Rotate, slightly overlapping. Length: About 1.1 cm. Width: About 1.2 cm. Shape: Orbicular. Apex: Rounded. Base: Attenuate. Margin: Entire. Texture, upper and lower surface: Smooth, glabrous. Color: When opening, upper surface: 62B to 65A; red purple-colored spot towards the base, 59A to 59B. When opening, lower surface: 65A; red purple-colored spot towards the base, 59A to 59B. Fully opened, upper surface: 62C to 65B; red purple-colored spot towards the base, 59B. Fully opened, lower surface: 62C; red purple-colored spot towards the base, 59B.

*Sepals.*—Quantity per flower: Five, fused at base. Arrangement: Rotate, star-shaped. Length: About 5 mm. Width: About 1.75 mm. Shape: Elliptic. Apex: Acute. Base: Cuneate, fused. Margin: Entire. Texture, upper and lower surfaces: Pubescent. Color, upper and lower surfaces: 137D.

*Peduncles.*—Length: About 30 cm. Diameter: About 2 mm. Angle: Erect to about 60° from vertical. Strength: Strong. Color: 143B.

*Pedicels.*—Length: About 1 cm. Diameter: About 0.5 mm. Angle: About 55 to 70° from vertical. Strength: Strong. Color: 143A to 143B.

*Reproductive organs.*—Stamens: Quantity per flower: Five. Anther shape: Broadly triangular; dorsifixed. Anther length: About 1.2 mm. Anther color: N25C. Pollen amount: Scarce. Pollen color: Close to N25C. Pistils: Quantity per flower: One. Pistil length: About 1 cm. Style length: About 9 mm. Style color: 59B to 59C. Stigma shape: Club-shaped. Stigma color: N144A. Ovary color: 138A.

*Fruit/seed.*—Fruit and seed development have not been observed.

Disease/pest resistance: Plants of the new Verbascum have not been noted to be resistant to pathogens or pests common to Verbascum.

Temperature tolerance: Plants of the new Verbascum are tolerant to temperatures from about −20 to 30° C.

It is claimed:

1. A new and distinct cultivar of Verbascum plant named 'Rosie', as illustrated and described.

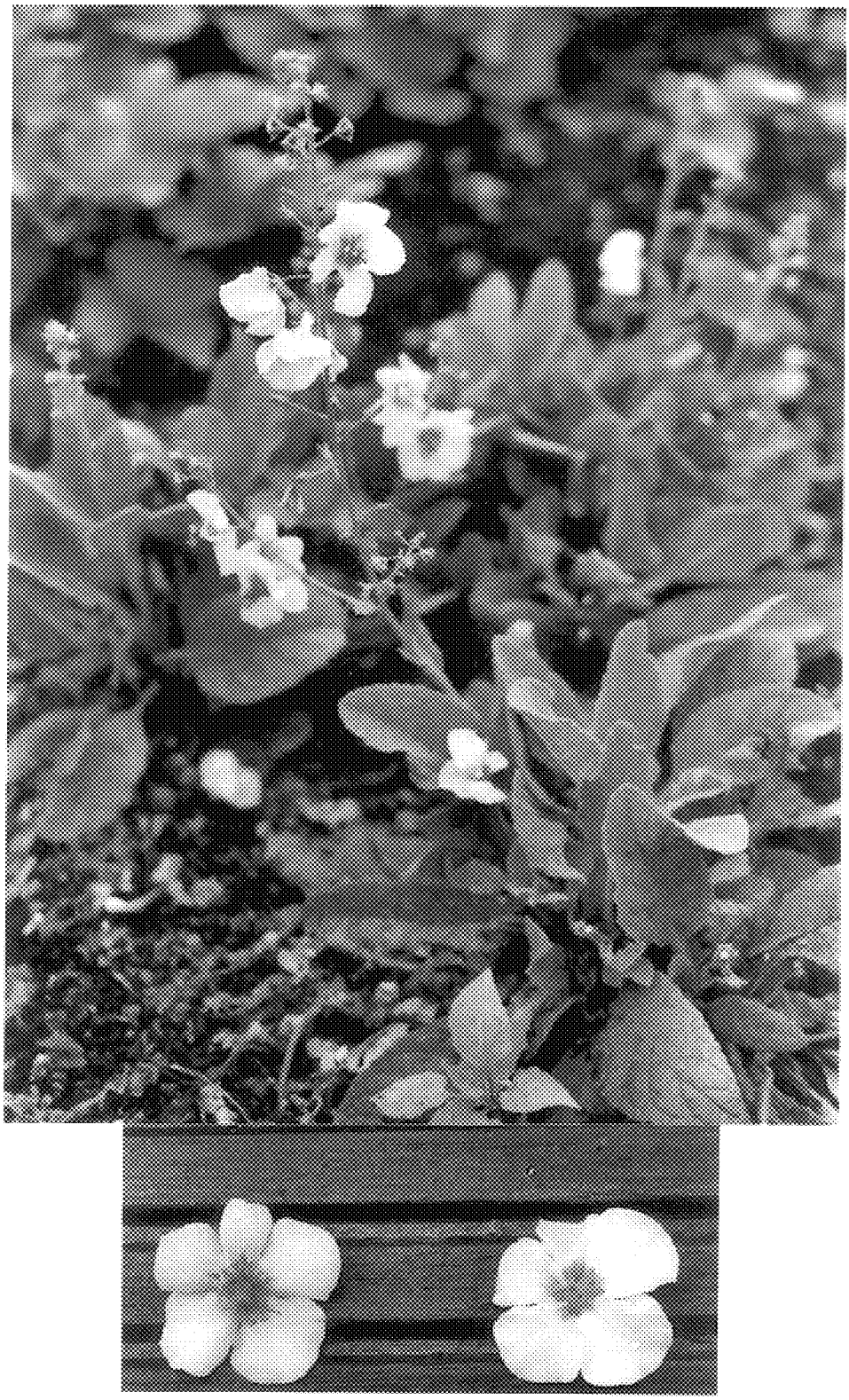

* * * * *